United States Patent [19]

Wong et al.

[11] Patent Number: 5,603,947
[45] Date of Patent: Feb. 18, 1997

[54] METHOD AND DEVICE FOR PROVIDING NICOTINE REPLACEMENT THERAPY TRANSDERMALLY/TRANSBUCCALLY

[75] Inventors: Ooi Wong, Fremont; Kathleen C. Farinas, San Francisco; Gary W. Cleary, Menlo Park; Chia-Ming Chiang, Foster City; Jun Xia, Redwood City, all of Calif.

[73] Assignee: Cygnus Terapeutic Systems, Redwood City, Calif.

[21] Appl. No.: 278,277

[22] Filed: Jul. 21, 1994

Related U.S. Application Data

[63] Continuation-in-part of Ser. No. 247,520, May 23, 1994, abandoned, which is a continuation of Ser. No. 89,971, Jul. 9, 1993, abandoned.

[51] Int. Cl.⁶ .................................................. A61F 13/00
[52] U.S. Cl. ........................ 424/448; 424/447; 424/449
[58] Field of Search ........................ 424/448, 449, 424/447

[56] References Cited

U.S. PATENT DOCUMENTS

| | | | |
|---|---|---|---|
| 4,496,853 | 8/1985 | Bannon | 326/87 |
| 4,758,434 | 7/1988 | Kydonieus et al. | 424/449 |
| 4,839,174 | 6/1989 | Baker | 424/447 |
| 4,877,618 | 10/1989 | Reed, Jr. | 428/448 |
| 4,943,435 | 7/1990 | Baker | 424/448 |
| 5,004,610 | 4/1991 | Osborne | 424/448 |
| 5,016,652 | 5/1991 | Rose | 131/270 |
| 5,064,654 | 11/1991 | Berner | 424/448 |
| 5,091,186 | 2/1992 | Miranda et al. | 424/448 |

FOREIGN PATENT DOCUMENTS

| | | |
|---|---|---|
| 0450986 | 10/1991 | European Pat. Off. . |
| 0469745 | 2/1992 | European Pat. Off. . |
| 0481443 | 4/1992 | European Pat. Off. . |
| 0484543 | 5/1992 | European Pat. Off. . |
| 0524776 | 1/1993 | European Pat. Off. . |
| 3438284 | 10/1984 | Germany . |
| 1197-435-A | 1/1988 | Japan . |
| 04077419-A | 7/1990 | Japan . |
| 91/03998 | 4/1991 | WIPO . |
| 91/16085 | 10/1991 | WIPO . |
| WO91/14463 | 10/1991 | WIPO . |
| 93/00057 | 1/1993 | WIPO . |

*Primary Examiner*—D. Gabrielle Phelan
*Attorney, Agent, or Firm*—Morrison & Foerster LLP

[57] ABSTRACT

A skin or buccal patch for providing nicotine replacement therapy which comprises a matrix type laminated composite in which the matrix is composed of a mixture of nicotine in a polymer wherein the amount of nicotine in the matrix, diffusion coefficient of nicotine in the matrix and the thickness of matrix are such that the release of nicotine is: (1) controlled by the patch; (2) rapid and at a relatively high flux over the prescribed wearing time of patch; and (3) such that a substantial proportion of the nicotine initially in the patch has been released at the end of the prescribed wearing time.

9 Claims, 13 Drawing Sheets

METHOD AND DEVICE FOR PROVIDING NICOTINE REPLACEMENT THERAPY TRANSDERMALLY/TRANSBUCCALLY

CROSS-REFERENCE TO RELATED APPLICATIONS

This application is a continuation-in-part of U.S. patent application Ser. No. 08/247,520 filed 23 May 1994 now abandoned which in turn is a continuation of U.S. patent application Ser. No. 08/089,971 filed 9 Jul. 1993 and now abandoned. The disclosures of these related applications are incorporated by reference herein.

DESCRIPTION

1. Technical Field

This application relates to transdermal/transbuccal nicotine replacement therapy. More particularly, it relates to a device for and a method of providing transdermal/transbuccal nicotine replacement therapy via a unique dosing regimen which is applicable to heavy smokers.

2. Background of the Invention

Nicotine replacement therapy is used to provide smokers with nicotine from sources other than cigarettes. It is employed as an aid to assist smokers to quit smoking or to sate smokers who wish to reduce smoking or who are temporarily prevented from smoking for legal and/or social reasons.

In nicotine replacement therapy, the nicotine is typically administered parenterally through a body membrane. In the case of administering nicotine via chewing gum, the nicotine is delivered via the mucosal membranes of the oral cavity (i.e., the buccal mucosa). Nasal administration involves transmitting the nicotine to circulation by passage through the nasal mucosa. Finally, in the case of transdermal administration, the nicotine is passed through the skin to the vessels of the circulatory system.

Nicotine replacement therapy patches should provide amounts of nicotine to the user that correspond to all or a significant proportion of that which the user was provided by smoking or other means of consumption. In addition, for safety purposes, it is desirable that the device (1) control the flux of nicotine through the skin (as opposed to the skin controlling the flux) and (2) have a relatively high degree of nicotine depletion over the prescribed dosing or wearing period. Also to reduce the likelihood of disturbing sleep, it is preferable that the patch release nicotine in a manner that results in low plasma levels of nicotine during normal sleeping hours.

Currently four different transdermal nicotine replacement therapy patches are available commercially in the U.S. Each of them is directed to provide nicotine replacement therapy for "light" to "medium" smokers. The four patches are: the NICOTROL® system; the NICODERM® system; the PROSTEP® system; and the HABITROL® system. The physician inserts for each of these products include graphs of nicotine plasma levels vs. time. The graph for the NICOTROL® 15 mg/day shows the levels reach about 13 ng/mL at about 4 hours and decline to about 7 ng/mL at 16 hours at which time the system is removed. Plasma levels then decay to about 2 at 24 hr. The graph for the 21 mg/day NICODERM® system (the largest) shows a rise from a base level of 12 ng/mL to about 22 ng/mL followed by a slow decline that reaches the base level of 12 ng/mL at 24 hours. The largest PROSTEP® system (22 mg/day) rises to about 16 ng/mL over 4 hours from a 5 ng/mL baseline and then exhibits a steady decline to the base level at 24 hours. Finally, the HABITROL® 21 mg/day system provides a plasma level that rises from a baseline of 11 ng/mL to just over 15 ng/mL at approximately 10 hours and then slowly declines from that peak down to the baseline.

None of these systems administers nicotine at levels that are suitable for treating heavy smokers.

DISCLOSURE OF THE INVENTION

One aspect of the invention is a laminated composite for providing transdermal or transbuccal nicotine replacement therapy to a person needing such therapy over a predetermined time period, t, comprising in combination:

(a) a nicotine impermeable backing layer; and (b) a matrix layer having a thickness, l, and comprising a mixture of a polymer and a sufficient amount of nicotine to provide said therapy, the nicotine having a diffusion coefficient D in the matrix layer, wherein the ratio $$\frac{Dt}{l^2}$$

is in the range of about 0.5 to 20 and wherein the composite controls the rate at which nicotine is administered from said matrix across the skin or buccal mucosa of the person over at least 50% of t and the average flux of nicotine from the matrix layer over t is greater than 50 µg/cm²/hr.

Another aspect of the invention is a method for providing transdermal or transbuccal nicotine replacement therapy to a person needing such therapy comprising affixing the above described laminated composite in diffusional relationship to the skin or buccal mucosa of the person.

MODES FOR CARRYING OUT THE INVENTION

As used herein the term "nicotine" includes nicotine free base and pharmaceutically acceptable salts of nicotine that are capable of transdermal/transbuccal administration.

As used herein, the term "nicotine replacement therapy" intends transdermal or transbuccal administration of nicotine which supplements or substitutes for the nicotine provided to an individual via smoking or other modes of nicotine consumption (e.g., chewing tobacco).

The term "heavy smoker" denotes a person whose smoking provides the smoker with an average daily dose of nicotine in the range of about 25 to about 75 mg.

The term "predetermined time period" intends the time period over which the laminated composite of the invention is designed to administer an effective amount of nicotine. This will generally correspond to the prescribed wearing time (i.e., the time period over which the composite is intended to be affixed to the skin). Naturally, the composite may be worn beyond the prescribed time period, but, because of the release kinetics of the composite only therapeutically insignificant amounts of nicotine are released after the prescribed wearing period. The prescribed wearing time will be in the range of 0.5 to 24 hr. In the case of composites that are intended to be worn in a once-a-day regimen to replace the normal daily amount of nicotine previously consumed by the wearer, the preferred prescribed wearing time will be approximately 24 hr. Correspondingly, in the case of composites that are intended to provide therapy over periods during which the wearer is legally or socially prohibited from smoking, the prescribed wearing time will be of significantly shorter duration, usually 1 to 10 hr. Further patches that are intended for buccal administration will usually be of shorter duration, typically 0.5 to 6 hr.

The devices of this invention are "monolith" or "matrix" type laminated composite structures in which the nicotine is contained within a matrix layer comprised of the nicotine blended homogeneously with a polymer carrier. Other materials such as plasticizers, permeation enhancers or nicotine sorption compositions may also be present in the matrix. Such additives may affect the diffusion coefficient of nicotine in the matrix or, when released from the matrix to the skin, alter the permeability of the skin to nicotine.

The diffusion coefficient (D) of nicotine in the matrix and the thickness (1) of the matrix affect the kinetics of the release of nicotine from the matrix. In this regard the diffusion coefficient of nicotine in the matrix will usually be in the range of about $1 \times 10^{-6}$ to $1 \times 10^{-12}$, more usually $1 \times 10^{-9}$ to $5 \times 10^{-7}$ cm$^2$/sec. $D/l^2$ is determined by first determining in vitro nicotine release (not through skin) from the device as described in Example 1, infra. The in vitro nicotine release data are analyzed according to "Controlled Release of Biologically Active Agents" by Richard W. Baker, Wiley Interscience (1987) page 51, equation 3.16. Only data up to 60% of the nicotine loading are included in the analysis. The diffusion coefficient is determined from the slope of the plot of the in vitro nicotine release (normalized by the nicotine loading) versus the square root of time. For systems such as those shown in FIG. 3 which have an additional adhesive layer, equation 3.16 should be used to determine an effective $D/l^2$. (Note that the Baker analysis of data involves drug release from two sides of a matrix. In release tests conducted on patches with an impermeable backing release only occurs from one side of the matrix. Thus, the thickness, l, used in Baker equation 3.16 should be replaced by 2×l, where l is the actual thickness of the matrix).

The thickness of the matrix layer will normally be in the range of 25 to 500 microns, more usually 50 to 350 microns.

As indicated previously, in the composites of this invention the ratio $$\frac{Dt}{l^2}$$

is in the range of about 0.5 and 20, preferably 0.75 to 10, and most preferably 0.75 to 5. One or more of D, l, and t may be varied within the ranges described above to obtain such a ratio.

Another distinguishing characteristic of the devices of the invention is that they, rather than the skin or buccal mucosa of the wearer, control the rate at which nicotine is administered to the wearer. The relative control by the device and by the skin/mucosa may be determined by standard in vitro diffusion tests in which the cumulative dose of nicotine (Ad) from the device directly into an aqueous sink is compared to the cumulative dose of nicotine from the device and through skin/mucosa into the aqueous sink (At). Such comparisons are described by Guy, R. H. and Hadgraft, J. in the International Journal of Pharmaceutics (1992) 82:R1–R6. Those comparisons permit one to determine the fractional control exerted by the device (Fd) which is equal to the cumulative dose of nicotine from the device and through skin into the sink divided by the cumulative nicotine from the device directly into the sink. Thus when these doses are equal Fd=1 and the device totally controls the delivery of nicotine to the wearer. Correspondingly, when Fd>0.5 the device exerts more control than the skin. For the purposes of the present invention the device is considered to control the release of nicotine when Fd is $\geq 0.5$ for >50% of the time period t. Control of the release rate of nicotine by the device rather than the skin/mucosa makes the invention devices safer to use in that the administration of nicotine is not subject to variability in skin/mucosa permeability from wearer-to-wearer or from site-to-site on the skin/mucosa of an individual wearer. In order to assure that the device controls the nicotine release, known skin permeation enhancers may be incorporated into the matrix and co-administered with the nicotine. Examples, without limitation, of enhancers that may be so used are those described or referenced in commonly owned U.S. Pat. No. 4,906,463.

Yet another characteristic of the invention patches is that they have a relatively high degree of nicotine depletion over the prescribed wearing period. This feature renders the devices safer to dispose of in the sense that after use the amounts of nicotine which they contain are less likely to cause injury to children or pets who may inadvertently ingest them. The degree of depletion may be quantified by comparing the cumulative amount of nicotine released (as determined by standard in vitro diffusion tests of nicotine released through skin into an aqueous sink over the prescribed wearing period, t) with the initial amount of nicotine contained in the device (sometimes referred to as "nicotine loading"). In the invention devices over about 40%, more usually about 50%, of the initial amount of nicotine is released within the first 50% of t. Usually at least about 50% of the initial amount of nicotine is released over the entire period t. Another aspect of the depletion kinetics of these devices is that the average flux of nicotine from the devices is much higher in the initial stage of the wearing period than in the latter stages of wearing. This reduction in flux may be quantitated by comparing the average flux over the last ⅓ of the time period t with the average flux over the entire period. In the patches of the invention the ratio of the average flux over the last ⅓ of t to the average flux over the entire period t is less than about 0.4 usually between 0.1 and 0.4. All currently available nicotine patches exhibit rates in excess of 0.4.

The initial amount of nicotine in the matrix layer will vary between about 2 and 100 mg with lower amounts in this range being used for shorter duration (i.e., 10 hr or less, 5–50 mg) or buccal embodiments (2–25 mg) of the device and higher amounts in the range (e.g., 50–100 mg) being used for once-a-day devices that provide replacement therapy to heavy smokers. In the case of devices for heavy smokers, the average flux of nicotine from the matrix layer over the time period t (measured in vitro by standard diffusion tests) will normally be greater than 50 μg/cm$^2$/hr, usually 60 to 125 μg/cm$^2$/hr.

The polymer carrier ingredient of the matrix layer is selected to provide the requisite diffusion coefficient, D, and desired partition coefficient. In this regard the properties of the matrix layer are more important than the type or class of polymer used as a carrier. That is the layer needs to provide a proper $Dt/l^2$ and have a low nicotine solubility (e.g., less than about 30% by weight) so that there is good partitioning of nicotine into the skin or provide an enhancer to reduce the resistance of the skin to nicotine permeation. Partition coefficients may be determined by placing a 50 micron thick nicotine-free matrix in a diffusion cell (the same cells as are described in Example 1, infra). A 6% solution of nicotine in water is used as the donor solution at a volume $\geq 1$ ml so that nicotine concentration in the donor solution remained constant. Samples are collected as in the flux studies of Example 1, infra. D and the nicotine concentration in the matrix in equilibrium with the donor solution can be obtained by fitting the data from the samples with equation 4.24 in "Mathematics of Diffusion", Crank, J., Clarendon Press, Oxford (1975) 2nd Ed. The partition coefficient can be calculated by dividing the nicotine concentration in the donor solution by the concentration in the film in equilibrium with the donor solution. A high partition coefficient (above about 1) indicates low solubility of nicotine in the matrix. As indicated previously, a high partition coefficient enables the device to control the release of nicotine. That is, a matrix with a low nicotine solubility/high partition coefficient will have a high thermodynamic activity, which in turn results in high concentration gradients and high nicotine flux through the skin.

It is also believed that the high flux embodiments of the invention have a relatively low potential for skin irritation. Skin irritation is believed to be associated with nicotine flux through the skin, the duration of exposure to the flux and the nicotine concentration at the skin/matrix interface. Because the devices of this invention release nicotine rapidly and then taper off (as opposed to relatively constant rate), the skin/mucosa is subject to high fluxes for a shorter duration (even though the average flux over the time period is high). Also, because the devices control nicotine release, there is no build up of nicotine at the skin/matrix interface.

It will be appreciated that D may be influenced by the concentration of nicotine in the layer or by the presence of other matrix ingredients such as plasticizers, permeation enhancers, or compounds that sorb nicotine. Also, if the matrix itself is to have adhesive properties, the polymer carrier must be a pressure sensitive adhesive. When the matrix is adhesive the basal surface of the layer provides the means by which the device is affixed to the skin or mucosa. If the matrix is not adhesive, other means (e.g., an underlying layer of adhesive, a peripheral ring of adhesive, an adhesive overlay or straps), must be used to affix the device to the skin. In all embodiments the matrix layer is in direct or indirect diffusional relationship to the skin or mucosa. In other words there is a diffusional pathway for nicotine to migrate from the matrix layer into the skin or mucosa. Examples of polymer carriers that may be used in the matrix layer are amine-resistant polydimethylsiloxanes (silicones), styrene-ethylene-butylene-styrene block copolymers (Kratons), styrene-isoprene block copolymers (Durotak), and polyisobutylenes.

In once-a-day embodiments in which (a) the matrix layer adheres directly to the skin and is made of a silicone adhesive and (b) the nicotine loading is high, it may be necessary to include solid, particulate additive(s) that sorb nicotine in order to improve the cold flow properties of the matrix. Examples of such sorptive materials are sodium starch glycolate, silica gel, and calcium, magnesium or aluminum silicate. These additives will normally constitute about 5 to 20% by weight of the matrix when they are present.

Figure 1:
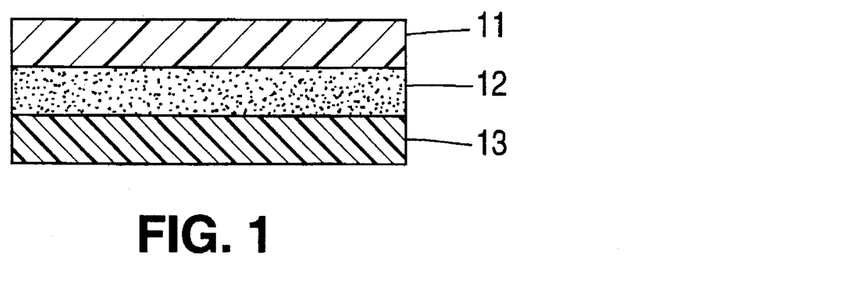
FIGS. 1–3 are cross-sectional diagrams (not to scale) of various embodiments of the invention.

FIG. 1 depicts the structure of one embodiment of a nicotine-containing transdermal patch of the invention. The device of FIG. 1 is a "monolith" type laminated composite structure (the nicotine is contained in a homogeneous adhesive matrix) which prior to wearing has three distinct layers: a conventional nicotine-impermeable backing layer 11 that defines the top surface of the device; an underlying matrix layer 12 comprised of a homogeneous mixture of nicotine in a pressure-sensitive adhesive polymer carrier as described supra; and a conventional removable release liner layer 13 that is removed before the device is placed on the skin. After release liner 13 is removed, the lower surface of the matrix layer is exposed and defines the basal surface of the device which is intended to be in direct adhesive contact with the skin.

The backing layer may be made of the nicotine-impermeable polymers or polymer-metal foil laminates that are used on the backing layers of the presently available nicotine replacement therapy patches. A laminate of polyester (Schüpbach) is a preferred backing layer material.

Figure 2:
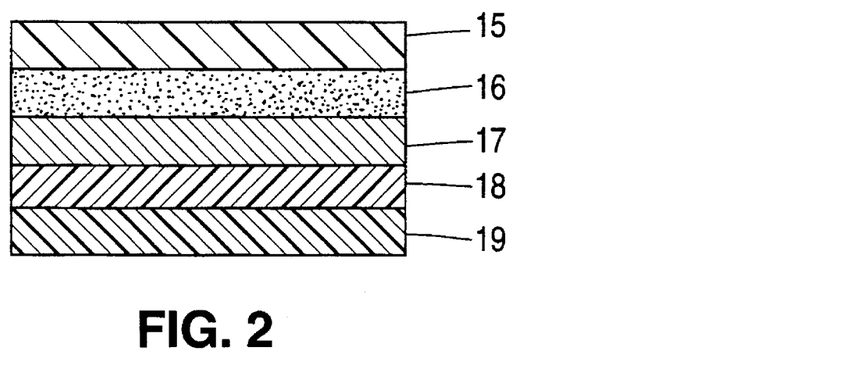

FIG. 2 shows an alternative device structure to that of FIG. 1. The device of FIG. 2 is a five-layer laminated composite of: a backing layer 15; an anchor adhesive layer 16; a nonwoven fabric layer 17; a matrix layer 18; and a release liner layer 19. The backing, matrix layer, and release liner layers are similar in composition and structure to the counterpart layers of the device of FIG. 1. Thus, the device of FIG. 2 differs from that of FIG. 1 by the presence of the anchor adhesive layer and the nonwoven fabric layer. Those layers are present solely for ease of manufacture and or improving the physical properties of the device as is known in the art (see U.S. Pat. No. 4,915,950). They do not materially alter or affect the release pattern of nicotine. The anchor adhesive layer is preferably made of the same adhesive as the adhesive of the matrix layer. When it is, layer 16, is in effect, part of the matrix layer. Conventional nonwoven fabrics may be used for layer 17.

Figure 3:
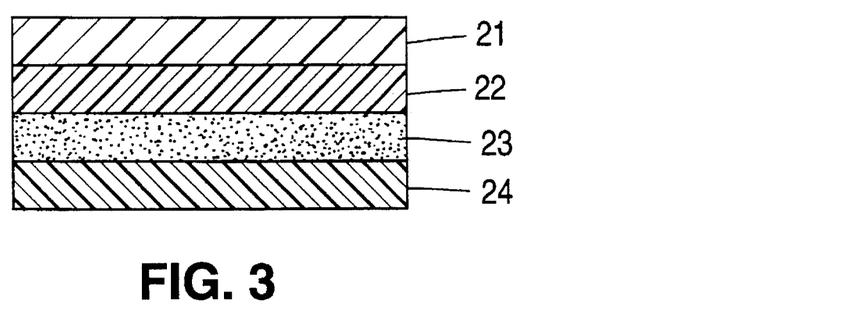

FIG. 3 depicts another alternative structure to that shown in FIG. 1. This device is similar in structure and composition to the device of FIG. 1, the differences being that the matrix layer has no adhesive properties (i.e., the polymer carrier is not a pressure sensitive adhesive) and the device includes an underlying adhesive layer. Accordingly, the device is a four-layer laminated composite of: a backing layer 21; a non-adhesive matrix layer 22; an adhesive layer 23; and a release liner layer 24. The backing layer and release liner layer perform the same functions as the counterpart layers of the device of FIG. 1. The matrix layer, however, being nonadhesive does not function as the means by which the patch adheres to the skin. Instead, the underlying adhesive layer 24 fulfills that function.

The diffusional surface area (i.e., the area of the basal surface of the device through which nicotine diffuses into the skin) will normally be in the range of 5 and 40 $cm^2$, inclusive. Devices of such surface area which provide the nicotine fluxes described above administer nicotine in amounts and rates that yield peak wearer plasma levels substantially above 25 ng/mL usually substantially above 35 ng/mL.

The devices from FIGS. 1–3 may be constructed using conventional equipment and procedures used in the fabrication of laminated composite transdermal drug delivery devices. See, for instance, U.S. Pat. No. 4,915,950.

The following examples further illustrate the invention. These examples are not intended to limit the invention in any manner. Unless indicated otherwise, percentages are by weight.

EXAMPLES

Example 1

A homogeneous 7% (based on weight of nicotine plus adhesive solids) mixture of nicotine in Dow Corning silicone adhesive 4201 was prepared by mixing an appropriate amount of nicotine and the adhesive plus solvent (heptane) in a rotary mixer for at least two hours. The mixture was spread evenly with a Gardener knife on a 1.3 mil thick backing layer (3M 1190 3M Scotchpak™) to a wet thickness of 25 mil. The resulting composite was dried in an oven for 60–80 minutes at 73° C. to remove solvent from the adhesive leaving a 350 micron thick matrix layer. A release liner layer (3 mil thick, Scotchpak™ 1022/3M) was laminated onto the nicotine/adhesive layer with a roller. The resulting three-layer laminated composite (corresponding to FIG. 1) was then cut in 15 cm² pieces. The pieces made each contained approximately 37 mg nicotine. The diffusion coefficient of nicotine in the matrix layer was determined to be $9.7 \times 10^{-8}$ cm²/sec.

These devices are intended to administer nicotine over a 16 hr period. Thus the ratio $$\frac{Dt}{l^2}$$

is calculated to be 4.6 for these devices.

In vitro nicotine skin flux studies were carried out on the above-described composites as follows.

Human cadaver epidermis was removed carefully from dermatoned full thickness skin after the skin had been heated in deionized water at 60° C. for one to two minutes. The stripped epidermis was placed between two polyethylene plastic sheets and kept in the refrigerator until use. Discs of the epidermis with a diameter of ⅝" were punched out with a die and tested for leakage. This was done by soaking the epidermis in water, then spreading it flat on a plastic sheet, and pressing the top of the epidermis lightly a few times with a piece of laboratory tissue. Leakage of the epidermis led to wet spots on the tissue.

The good epidermis disc was placed on top of the receiver cell of a modified Franz vertical diffusion cell assembly. A small magnetic stir bar was inserted through the sampling port into the donor cell compartment. Composites of the same size as the diffusion cell (0.71 cm²) were cut. (The sizes should be the same to avoid contributions from lateral diffusion.) The release liner from the composites was removed and the resulting two-layer composite was placed onto the epidermis. The diffusion cell assemblies were then clamped together and transferred to a skin permeation room (controlled at 32° C.). The receiver cell compartments were filled with 8.0 ml of the isotonic phosphate buffer of pH 7.0. At appropriate sampling time points, a 1.0 ml sample was removed from the receptor compartment followed by replacement of 1.0 ml of fresh buffer.

The concentration of nicotine in each sample was assayed by an HPLC analytical method. The HPLC apparatus used included a Perkin Elmer autosampler, ISS-200, a Perkin-Elmer pump 410B10, and a Perkin Elmer diode array detector LC-235. The column was μBondapack (30 cm×3.9 mm), C18, with particle size of 10 microns obtained from Waters. A guard column was used in conjunction with the column. The mobile phase contained 0.25M dodecyl sodium sulphate: 1M sodium acetate: water: acetonitrile (8:10:612:370) with a pH of about 3.5. The detection wavelength was set at 254 nm. The mobile phase flow rate was 2.0 ml/min and the sample injection volume was 25 μl. The retention time of the nicotine peak in the chromatograms was 3 to 4 minutes. The actual concentration of nicotine was directly interpreted from a standard curve constructed for each experimental run using known nicotine solutions.

Correspondingly in vitro drug release (not through skin) studies were made as follows.

Convex screen patch holder: (The design of the convex screen patch holder is described in Hadgraft, J., et al., Int J Pharm (1991) 73:125–130.) Following the removal of the patch release liner, the test patch was directly attached to the apex of the convex screen of the holder, with its drug release adhesive surface facing upwards. The assembly was then slowly dropped to the bottom of a glass vessel. The convex screen patch holder is designed to fit the bottom of a glass vessel relatively snugly and thereby hold the patch in position.

Drug release apparatus and procedures: Drug release from the test patch was conducted with a six-spindle USP Apparatus 5 employing glass vessels (Hanson Research Corporation, Chatsworth, Calif.). The distance between the center of the drug release surface of a patch and the bottom edge of a paddle was adjusted to 2.5 cm. The paddle speed was set at 50 rpm and the glass vessels were filled with 600 ml of deaerated, 0.025N HCl. This volume of receptor fluid is necessary to keep the released nicotine concentration low at a close-to-sink condition throughout the entire study while not over-diluting the medium. The receptor fluid was maintained at 32°±0.3° C. using a solid-state temperature control (Hanson Research). Aliquots of 1 ml samples were collected without filtering and replacement at 1, 2, 4, 6, 8, 12, 16 and 24 hr and the samples were analyzed for nicotine content using an HPLC system. The apparatus was calibrated using USP prednisone and salicylic acid calibrators before, and after, the drug release studies.

HPLC analysis of nicotine: The HPLC system consisted of a high-pressure pump (model 510, Waters, Division of Millipore Corporation, Bedford, Mass.), an auto injector/auto sampler (WISP 710B, Waters), a variable wavelength UV detector (Spectroflow 783, Kratos Analytical Instruments, Ramsey, N.J.) and an integrator/recorder (SP 4290, Spectra-Physics Analytical, San Jose, Calif.). A 50 μl sample was injected and analyzed using a Waters μBondapack C18 reversed phase column (300×3.9 mm) at ambient temperature. The mobile phase used was a mixture of 0.25M sodium dodecyl sulphate:1M sodium acetate:water:acetonitrile (8:10:612:370) with a flow rate of 2.0 ml/min and the UV detection was set at 254 nm.

The standard curve was constructed by plotting the peak area against the concentration using three different levels of nicotine standard solutions in duplicate injections. The relative standard deviations (RSD's), which were the ratios of standard deviations to the mean values, for these standards were less than 2% in the present study. The nicotine concentration in each sample was determined from its peak area with reference to the standard curve and the accumulative amount of nicotine released from a patch at the nth time point ($Q_n$) was calculated from the following relationship:

$$Q_n = C_n \times [V_R - V_S \times (n-1)] + \sum_{i=0}^{n-1} V_S \times C_i$$

where $C_n$ and $C_i$ are the nth and the ith term of the sample concentration, respectively, $V_R$ and $V_S$ are the receptor and the sample volume, respectively. Based on the patch size, the amount of nicotine released per unit drug diffusional area (mg/cm²) at each time point was determined.

Figure 4:
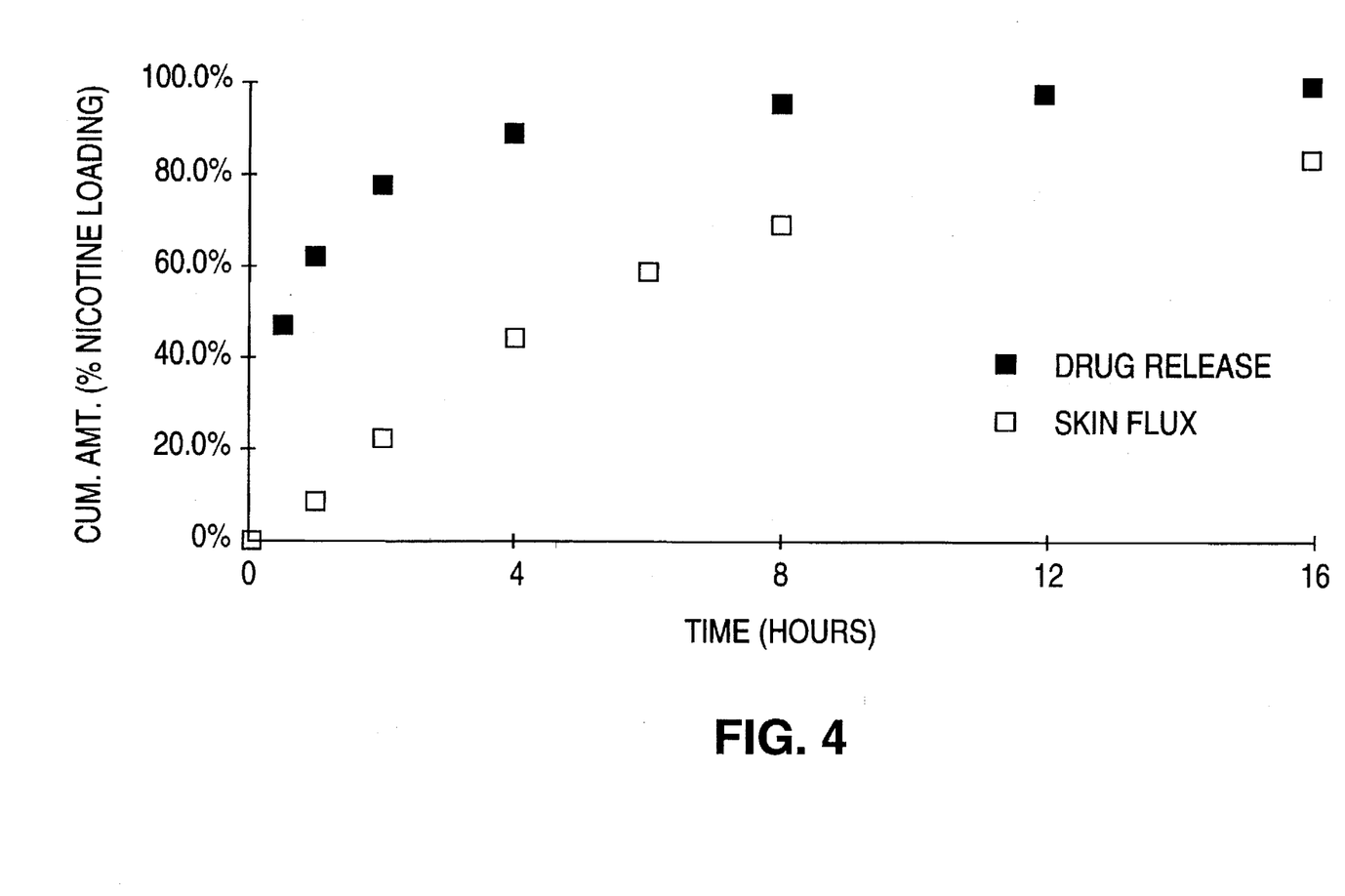
FIGS. 4–15 are graphs of the test data described in the examples, infra.
Figure 5:
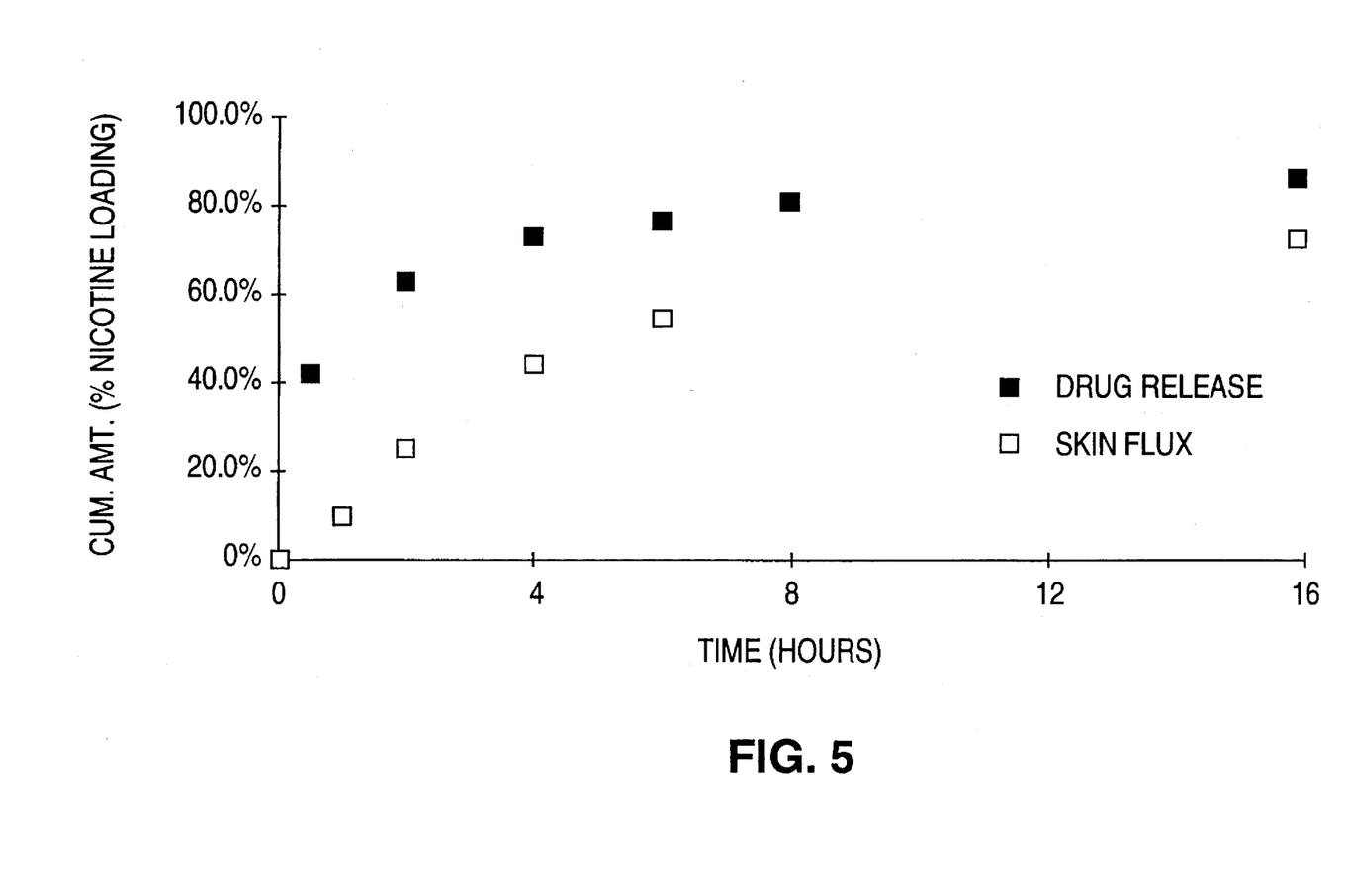
Figure 6:
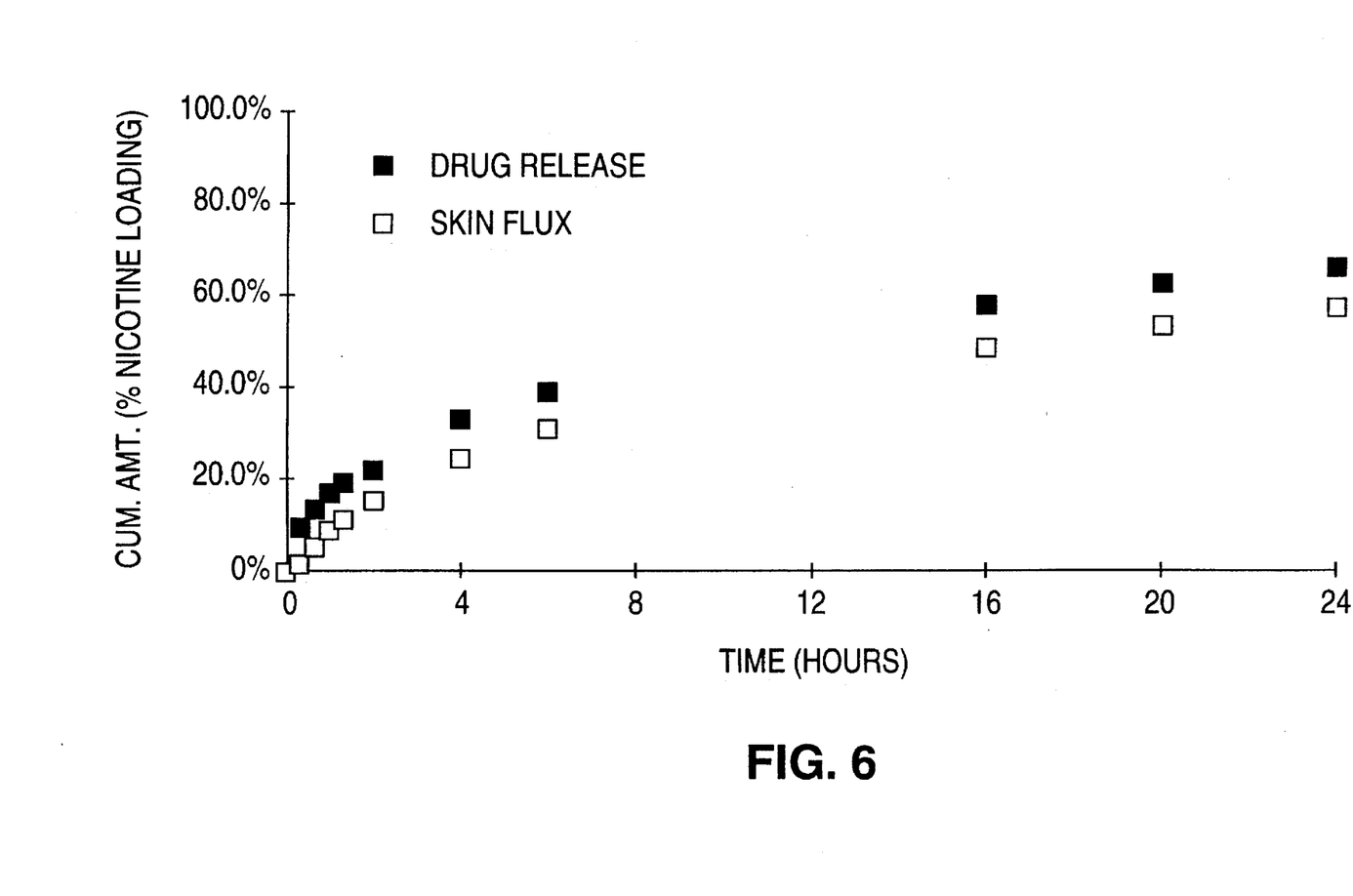
Figure 7:
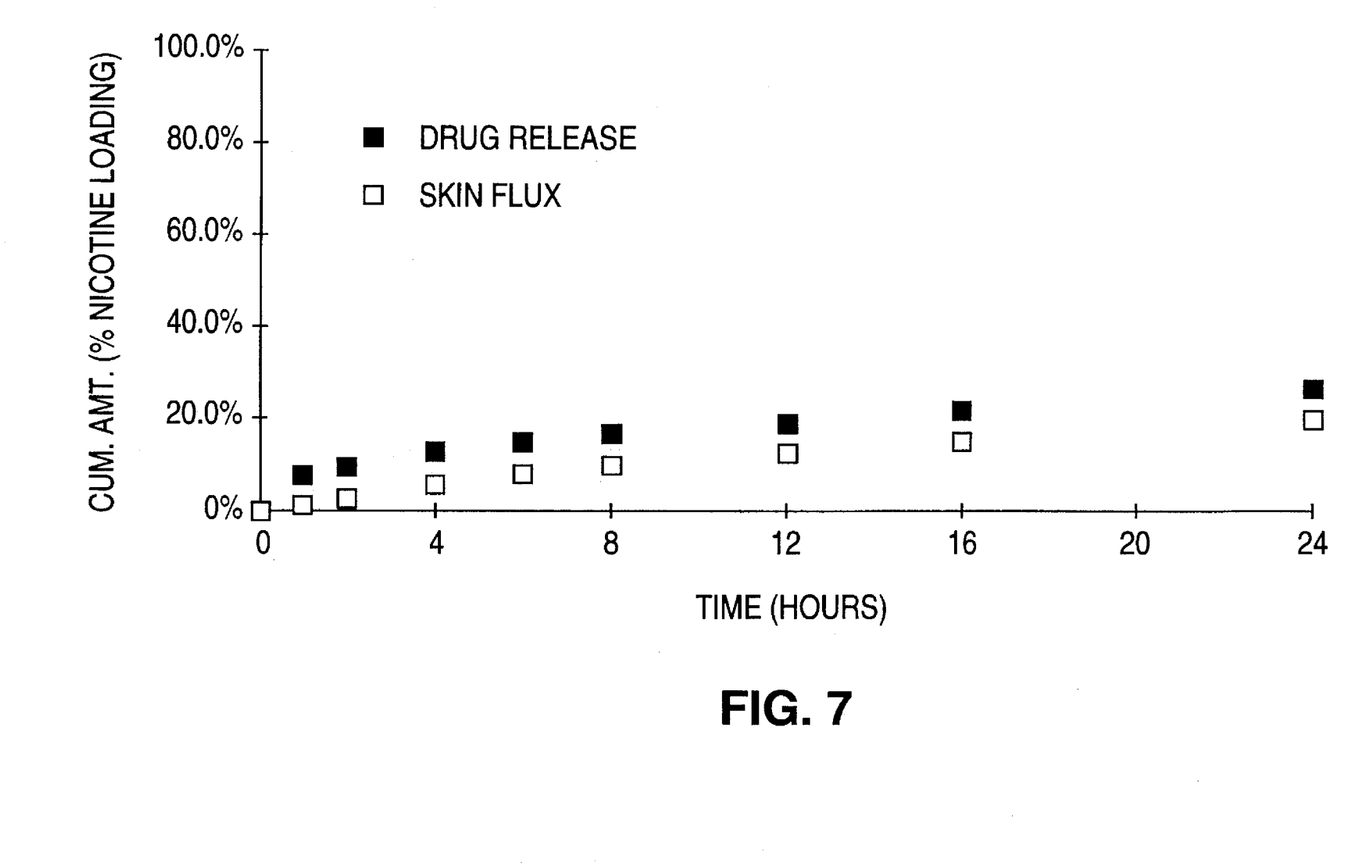
Figure 8:
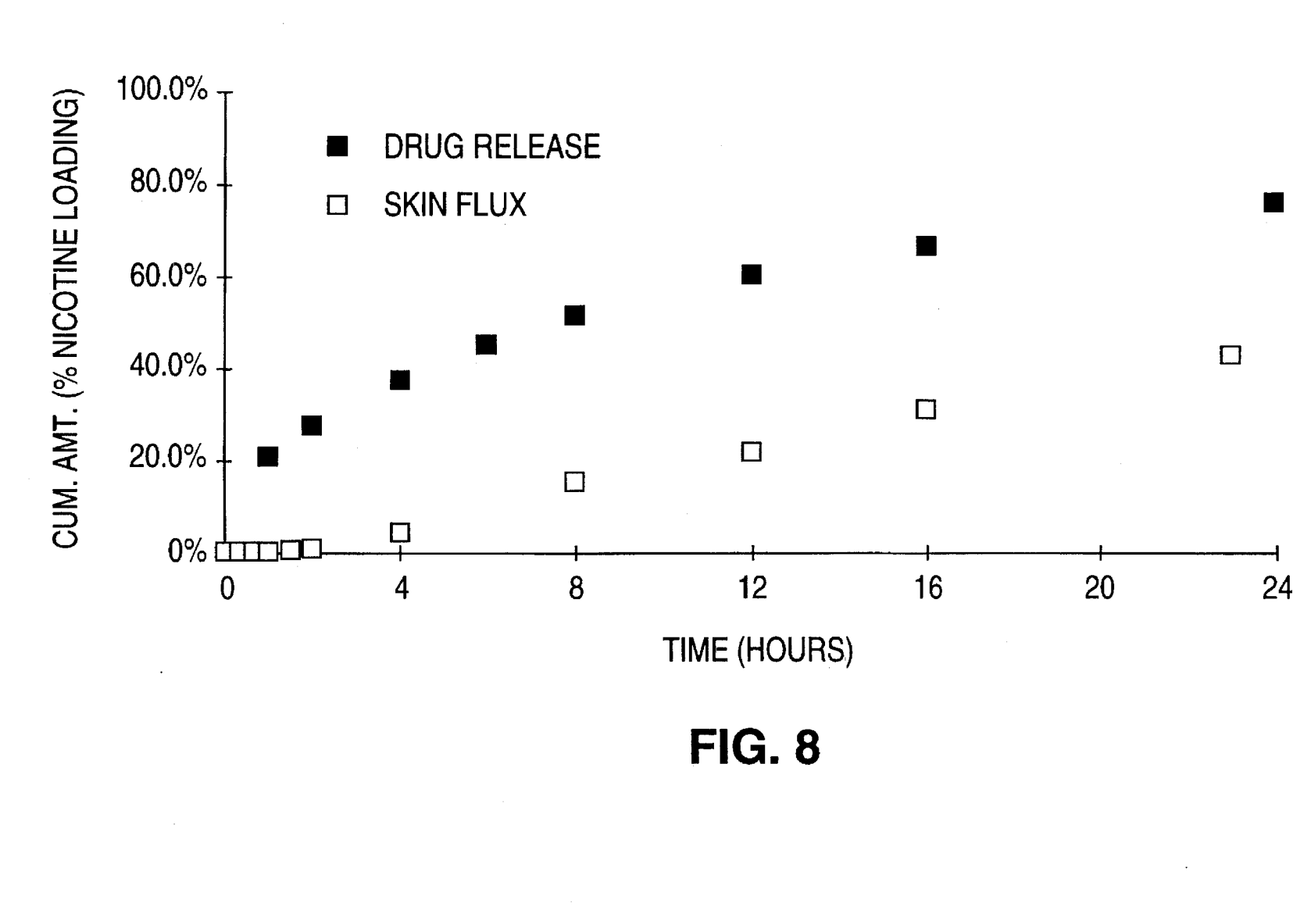
Figure 9:
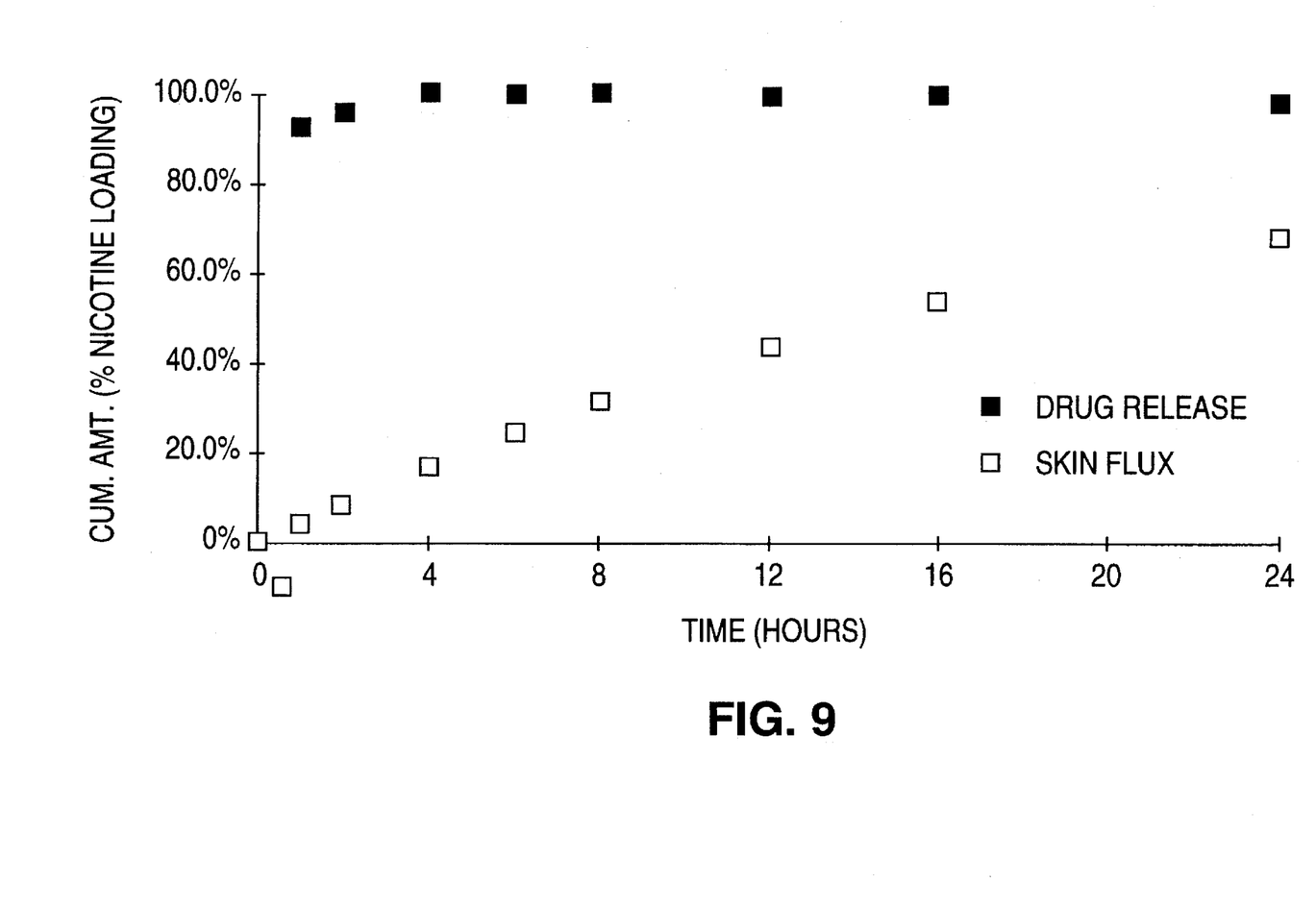

These plots are shown in FIG. 4.

Example 2

Devices of the general structure of FIG. 2 were prepared as follows. A homogeneous mixture of 10% (based on the weight of silica gel plus adhesive) silica gel (W. R. Grace 63FP) in Dow Corning silicone adhesive 4201 was prepared by mixing appropriate amounts of silica gel and the adhesive plus solvent (heptane) in a rotary mixer for at least two hours. This mixture was coated onto a release liner layer (Scotchpak™ 1022/3M) and a 100% polyester nonwoven fabric (3.4 mg/cm² Veratec Novonette) was laminated onto the adhesive layer and the assembly was dried in an oven at 70° C. for ½ hr.

The silica gel/adhesive mixture was also coated onto a 0.6 mil thick backing layer (Schüpbach) and the resulting assembly was dried in an oven at 70° C. for ½ hr.

Nicotine was deposited onto the nonwoven fabric of the release liner/adhesive/fabric assembly in a uniform pattern at 2.8 mg/cm². The backing layer/adhesive assembly was then laminated onto the fabric. The resulting matrix layer (the combined adhesive layers) was 350 microns thick. The laminated composite was cut into 30 cm² pieces, with each piece containing approximately 80 mg nicotine. The diffusion coefficient of nicotine in the matrix layer was determined to be $3.4 \times 10^{-8}$ cm²/sec. These composites are intended to administer nicotine over a 16 hr period. Thus, the ratio $$\frac{Dt}{l^2}$$

for these composites was calculated to be 1.6.

In vitro nicotine release and skin flux studies were carried out on this composite as in Example 1. For comparison, similar studies were carried out on the commercially available NICOTROL®, NICODERM®, HABITROL®, and PROSTEP® devices. FIGS. 5 to 9 are graphs of the results of these tests. The cumulative dose (through skin) from the composite of this example was significantly greater (approximately 50 mg) than the cumulative dose (through skin) from any of the four commercially available devices (maximum approximately 20 mg). Also as shown the release (through skin) was more rapid from the device of this example than any of the commercial devices.

Figure 10:
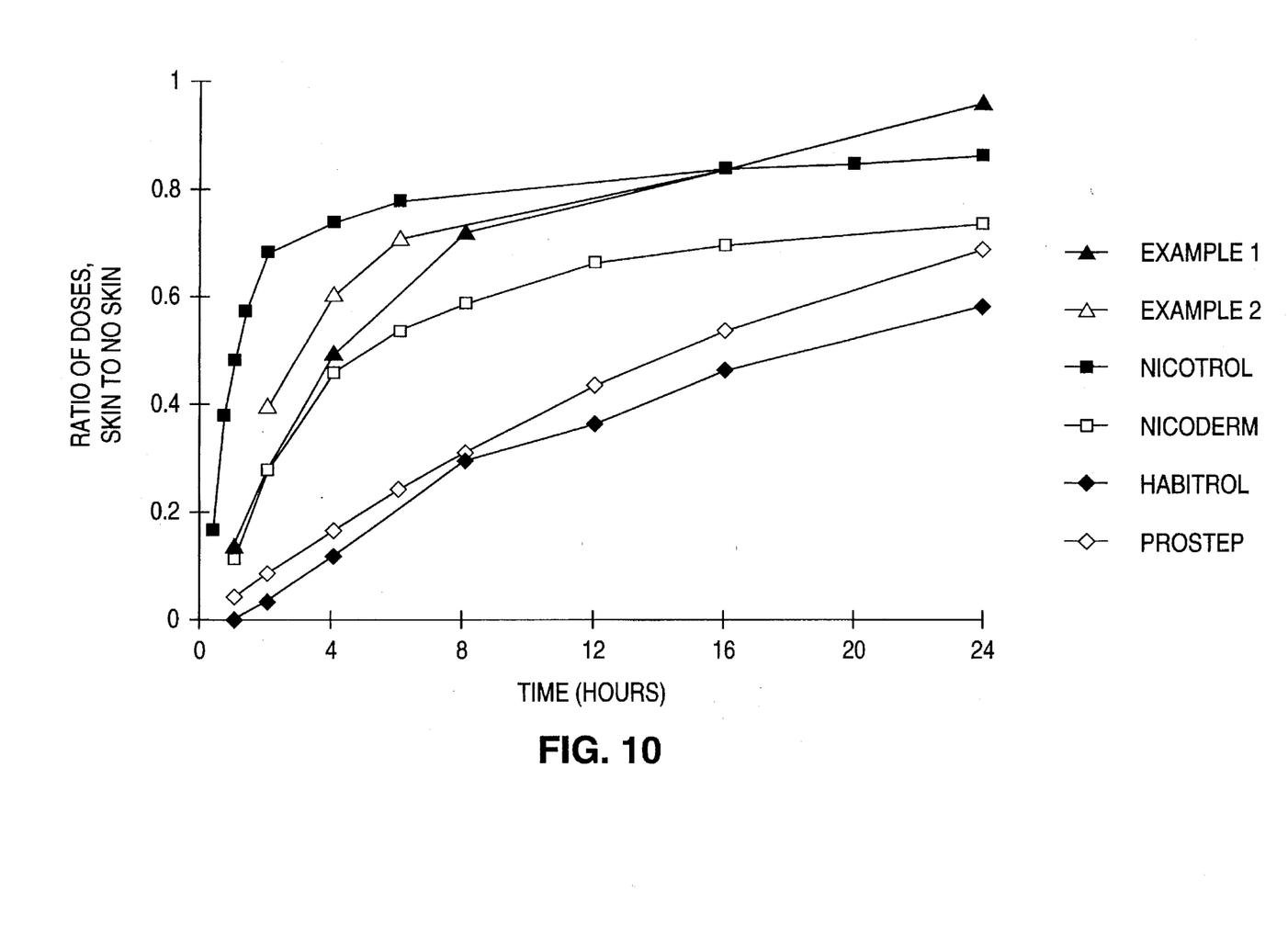

The ratios of doses (skin:no skin) for all the devices were calculated at various times and plotted (FIG. 10). These plots illustrate the extent to which the devices control the delivery of nicotine. As shown, the device of this example exerts more control than three of the four commercial devices. Also, these data show that the device of this example releases a greater proportion of its initial loading of nicotine than 3 of the 4 (PROSTEP® also releases 70% of loading) commercial devices.

Figure 11:
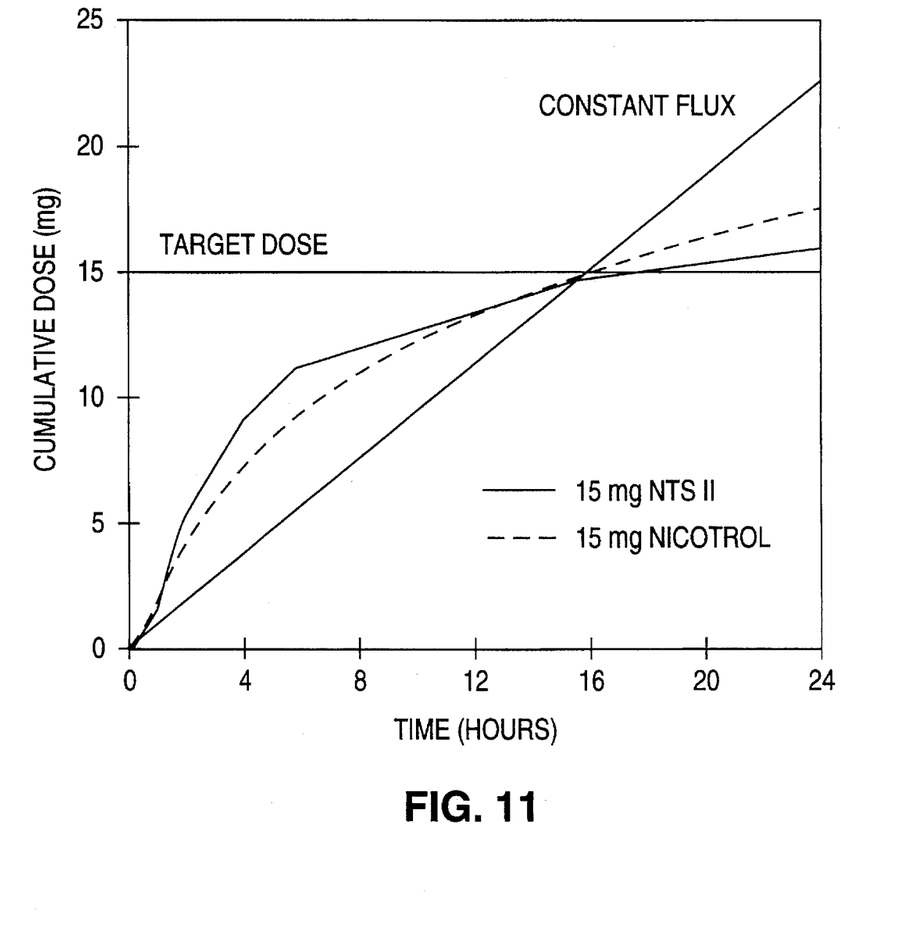

Cumulative dose plots were made to compare the performance of a device of Example 2 (designated NTS II) and a NICOTROL® device. FIG. 11 shows these plots with the size of the NTS II normalized to approximately 7.5 cm² to correspond to the dose provided by the NICOTROL® device. As shown the invention device delivers nicotine more rapidly and tapers off earlier than the NICOTROL® device. Also, in the 16–24 hr period, the invention device delivers less nicotine than the NICOTROL® device.

Example 3

A homogeneous mixture of 5.4 g of nicotine and 45 g of a hot melt adhesive (Durotak 34-4277) was prepared by blending these ingredients in a torque rheometer for approximately 15 min. The mixture was coated to a thickness of 4 mil (100 microns) onto a fluorocarbon-coated polyester release liner film (3M 1022 3 mil). This assembly was then laminated to a polyester backing film (Schüpbach backing material, 0.6 mil thick).

The diffusion coefficient of nicotine in the adhesive was determined to be $3 \times 10^{-9}$ cm²/sec. The device was designed to deliver nicotine for 16–24 hr. Accordingly the ratio $$\frac{Dt}{l^2}$$

for this composite is calculated to be 1.7 (for 16 hr).

Figure 12:
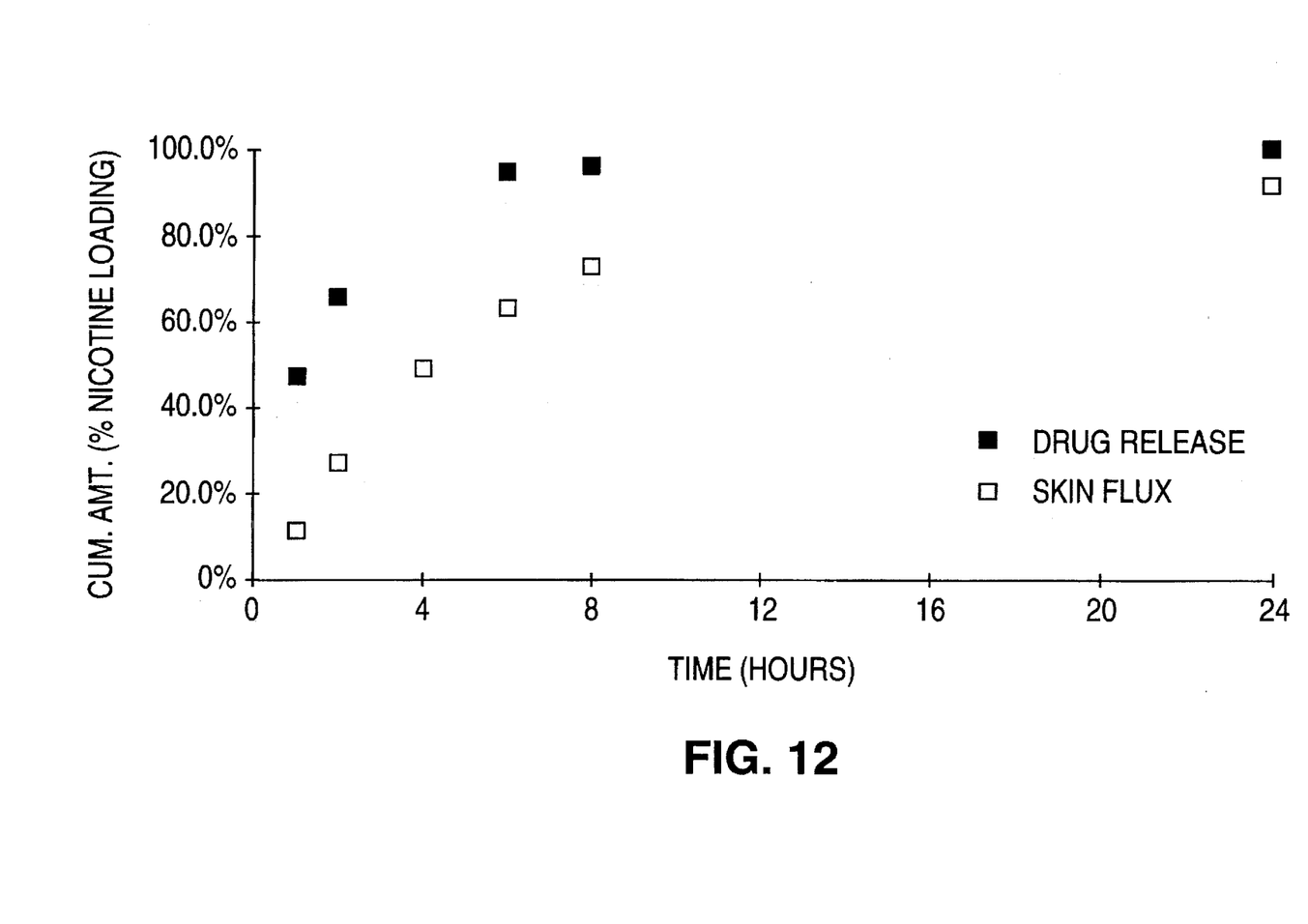

In vitro nicotine release and skin flux studies were carried out on these composites as in Example 1. FIG. 12 is a plot of the results of these tests.

Example 4

Figure 13:
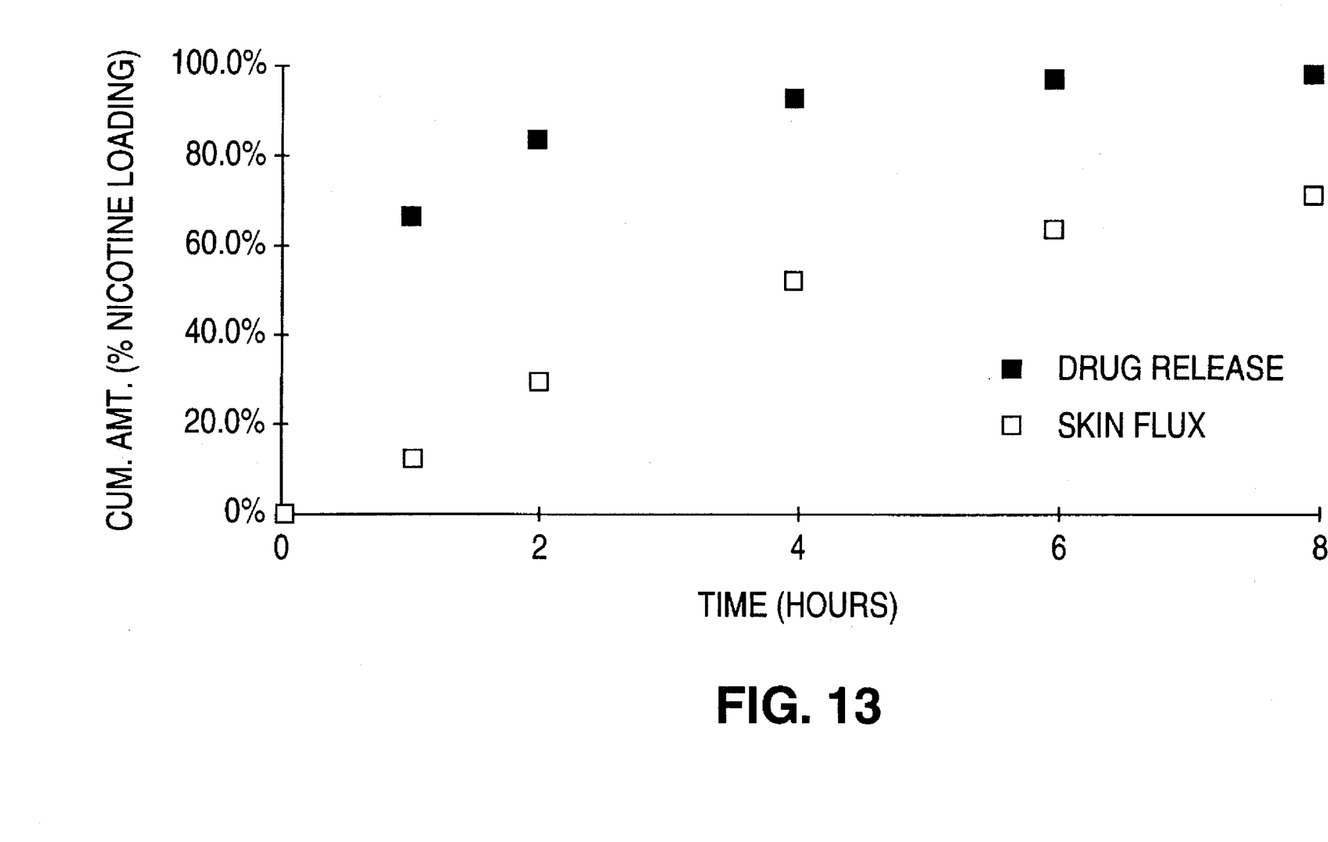

Laminated composites were prepared as in Example 3 except that the matrix was 2 mil (50 microns) thick. FIG. 13 gives plots of the nicotine release and skin flux data for this composite. The device was designed to deliver for 8–10 hr.

Example 5

Devices of the general structure of FIG. 2 were prepared as follows. A homogeneous mixture of 10% (based on the weight of silica gel plus adhesive solids) silica gel (W. R. Grace 63FP) in Dow Corning Silicone adhesive 4201 was prepared using a drive mixer with impeller and shaft. The adhesive mixture is coated onto a release liner layer (Scotchpak™ 1022/3M) by means of a coating knife. The adhesive solvent (heptane) was evaporated in a drying oven with three zones, spending approximately 4.5 minutes in each zone with temperatures set at ambient, 250° C. and 300° C. The exposed dried adhesive layer was laminated under uniform roll pressure to the backing film (0.6 mil Schupbach) to form the backing laminate, or to the nonwoven fabric (3.4 mg/cm² Veratec Novonette) to form the nonwoven laminate. The final dried adhesive weight of each laminate was approximately 20 mg/cm², corresponding to a thickness of 175 microns. After the backing and nonwoven laminates were combined as described below, the total amount of adhesive in the final system was approximately 40 mg/cm², or 350 microns.

Nicotine was applied onto the nonwoven laminate via a fluid delivery system in a uniform pattern at approximately 2.6 mg/cm². The backing laminate was laminated to the nicotine treated nonwoven laminate under uniform roll pressure. Systems (20 cm²) were die-cut from the final laminate using a rotary die. Each final system was placed between two layers of pouch stock (Jefferson Smurfit) and the pouch stock was sealed on all edges.

Figure 14:
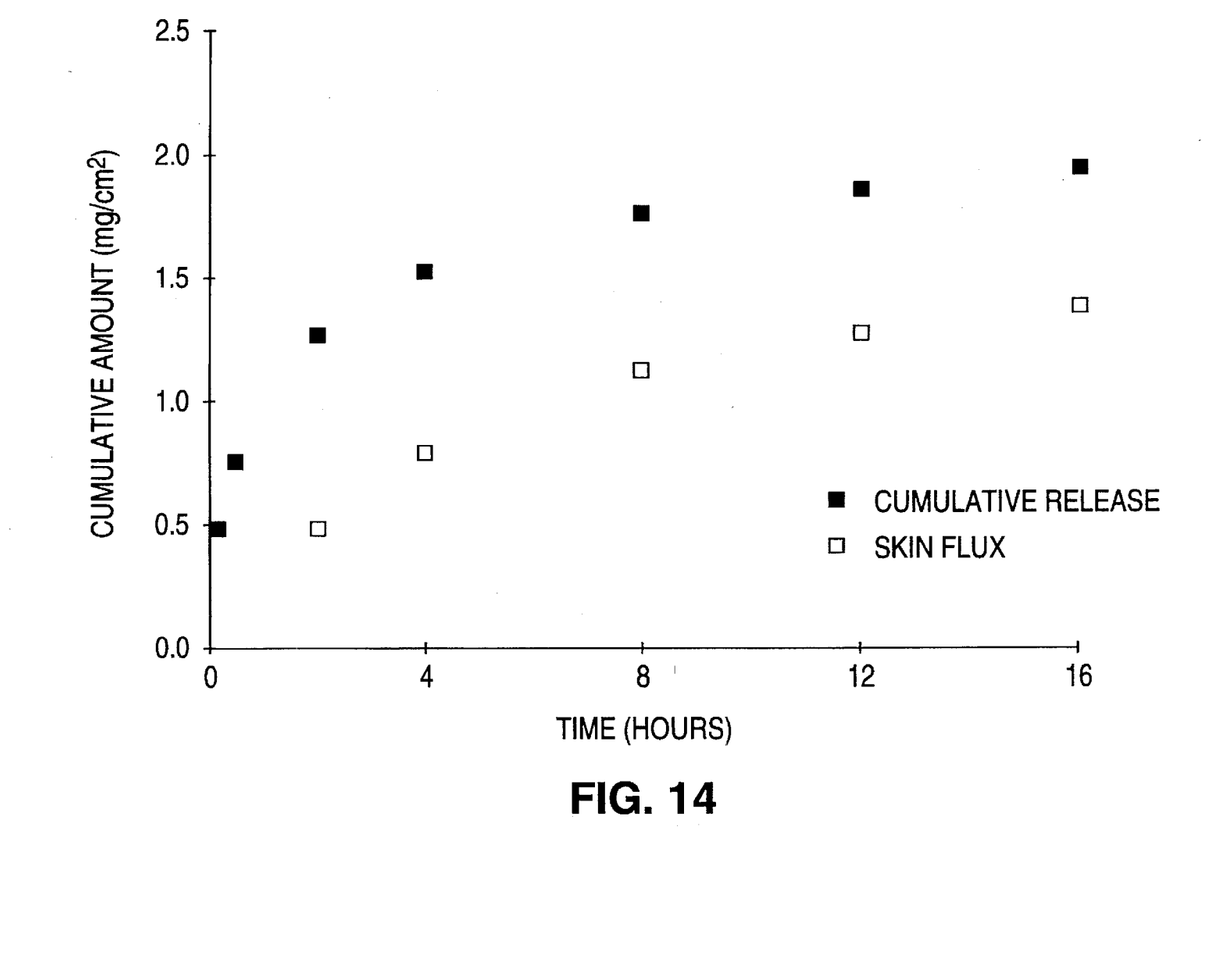

In vitro nicotine release and skin flux studies were carried out as in Example 1 except that the exact same patches were used for the two tests. This was accomplished by punching 0.71 cm² samples for the skin flux study out of the center of the patches and using the remainder of the patches for the release study. This device was designed to deliver for 16 hours and has a $Dt/l^2$ of 1.6. FIG. 14 displays the results of these studies. The ratio of doses (skin: no skin) is approximately 0.6 at eight hours. In addition, more than 40% of the initial nicotine loading is delivered at this time. The average flux of nicotine over 16 hours for the device of this example was approximately 85 µg/cm²/hr.

Example 6

Laminated composites were prepared as in Example 5 except for the following differences. A homogeneous mixture of 15% (based on the weight of silica gel plus adhesive solids) silica gel (W. R. Grace 63FP) in Dow Corning Silicone adhesive 4201 was prepared. The final dried adhesive weight of each laminate was approximately 15 mg/cm$^2$, corresponding to a thickness of 130 microns. After the backing and nonwoven laminates were combined, the total amount of adhesive in the final system was approximately 30 mg/cm$^2$, or 260 microns. Systems (30 cm$^2$) were die-cut from the final laminate using a rotary die.

Figure 15:
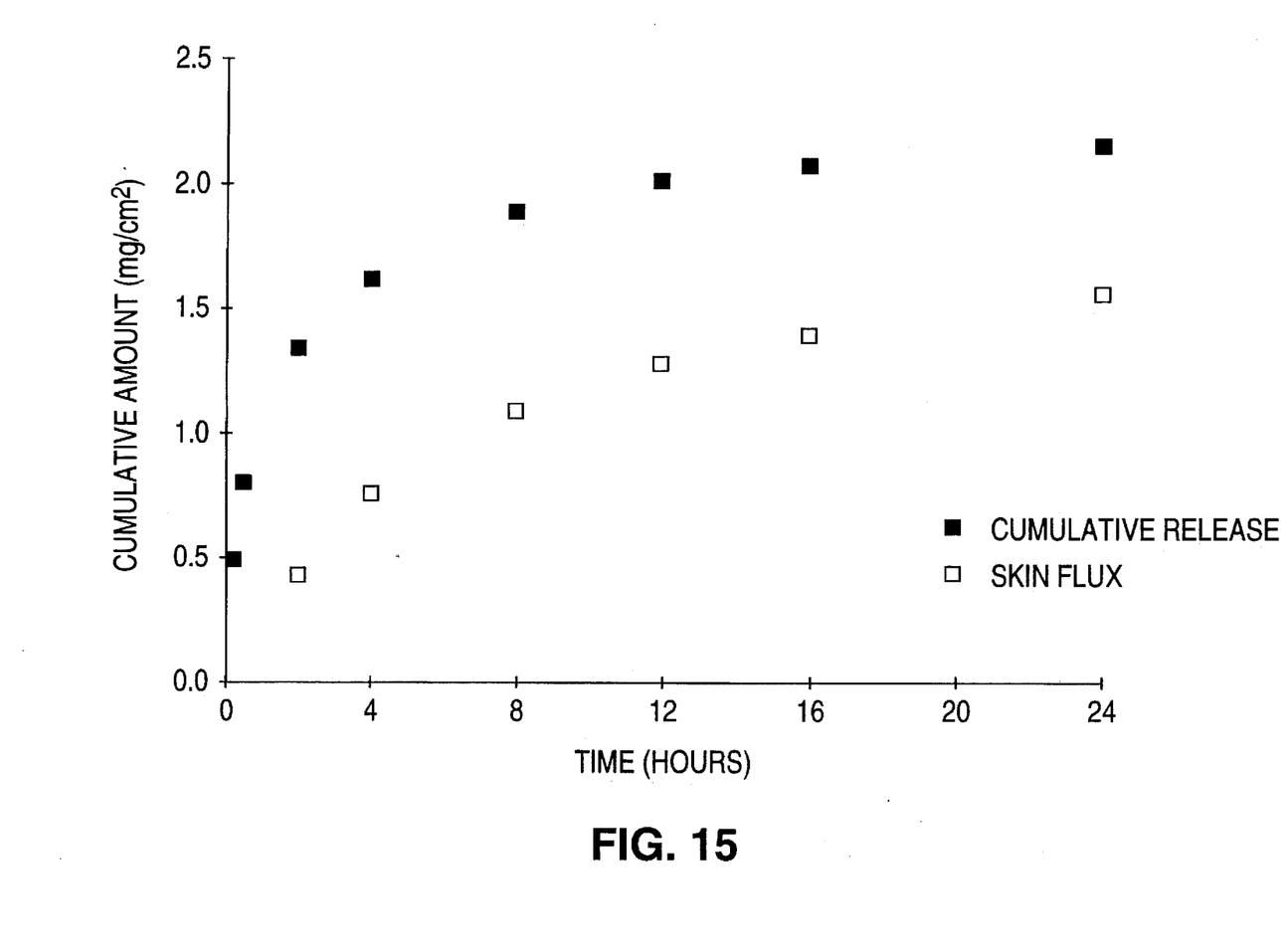

In vitro nicotine release and skin flux studies were carried out as in Example 5. This device was designed to deliver for 24 hours and has a $Dt/l^2$ of 2.6. FIG. 15 displays the results of these studies. The ratio of doses (skin: no skin) is approximately 0.6 at twelve hours. In addition, approximately 50% of the initial nicotine loading is delivered at this time. The average flux of nicotine over 24 hour for the device of this example was approximately 60 µg/cm$^2$/hr.

Modifications of the above-described modes for carrying out the invention that are obvious to those of skill in the field of transdermal drug delivery are intended to be within the scope of the following claims.

We claim:

1. A laminated composite for providing transdermal/transbuccal nicotine replacement therapy to a person over a predetermined time period, t, comprising in combination:
   (a) a nicotine-impermeable backing layer; and
   (b) a matrix layer having a thickness l and comprising a mixture of a sufficient amount of nicotine to provide said therapy and a polymer, the nicotine having a diffusion coefficient, D, in the matrix layer, wherein the ratio $$\frac{Dt}{l^2}$$

is in the range of about 0.5 to 20 and wherein the composite controls the rate at which nicotine is administered across said skin or mucosa over at least 50% of t and the ratio of the average flux of nicotine from the matrix layer over the last ⅓ of time period t to the average flux of nicotine from the matrix over the entire time period t is less than about 0.4.

2. The laminated composite of claim 1 wherein the polymer is a pressure-sensitive adhesive polymer and the matrix layer defines the basal surface of the composite when the composite is affixed in diffusional relationship to the skin of the person.

3. The laminated composite of claim 1 wherein the composite includes a nicotine-permeable pressure sensitive adhesive layer that underlies the matrix layer and defines the basal surface of the composite when the composite is affixed in diffusional relationship to the skin of the person.

4. The laminated composite of claim 1 wherein t is in the range of 0.5 and 24 hours, inclusive, D is in the range of $1\times10^{-9}$ and $5\times10^{-7}$ cm$^2$/sec, inclusive, and l is in the range of 25 and 500 microns, inclusive.

5. The laminated composite of claim 1 wherein $$\frac{Dt}{l^2}$$

is in the range of 0.75 to 5.

6. The laminated composite of claim 1 wherein over about 50% of said amount of nicotine is released from the composite within the time period t.

7. The laminated composite of claim 1 wherein the polymer is a pressure sensitive silicone adhesive and the mixture includes a solid particulate compound that sorbs nicotine.

8. The laminated composite of claim 7 wherein t is approximately 24 hr, l is approximately 260 microns, said amount is approximately 75 mg, the solid particulate compound that sorbs nicotine is silica gel and the silica gel constitutes approximately 15% by weight based on the combined weight of the dried adhesive silica gel mixture.

9. A method for providing transdermal or transbuccal nicotine replacement therapy to a person needing such therapy comprising affixing the laminated composite of claim 1 in diffusional relationship to the skin or buccal mucosa of the person.

* * * * *